United States Patent
Kang et al.

(10) Patent No.: US 7,763,694 B2
(45) Date of Patent: Jul. 27, 2010

(54) DIOL (METH) ACRYLATE COMPOUND HAVING URETHANE BOND, METHOD FOR PRODUCING THE SAME, AND POLYMER THEREOF

(75) Inventors: Eui-chul Kang, Tsukuba (JP); Atsuhiko Ogura, Tsuchiura (JP); Shingo Kataoka, Tsukuba (JP); Takashi Iwata, Fukuoka (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 12/631,049

(22) Filed: Dec. 4, 2009

(65) Prior Publication Data

US 2010/0081779 A1    Apr. 1, 2010

Related U.S. Application Data

(62) Division of application No. 12/478,189, filed on Jun. 4, 2009, now Pat. No. 7,649,105, which is a division of application No. 11/259,543, filed on Oct. 25, 2005, now Pat. No. 7,557,239.

(30) Foreign Application Priority Data

Oct. 27, 2004    (JP)    ............................. 2004-312432

(51) Int. Cl.
C08F 20/26    (2006.01)
C08F 34/02    (2006.01)
C08F 20/58    (2006.01)

(52) U.S. Cl. ........................ 526/320; 526/270; 526/301; 526/304; 526/333

(58) Field of Classification Search ................. 526/270, 526/301, 304, 320, 333
See application file for complete search history.

(56) References Cited

U.S. PATENT DOCUMENTS 7,374,863 B2    5/2008   Sugasaki et al.
2007/0148121 A1   6/2007  Fukui et al.

FOREIGN PATENT DOCUMENTS

JP    2003-212954 A    7/2003
JP    2003-315998 A    11/2003

OTHER PUBLICATIONS

Patent Abstracts of Japan for JP2003-212954 published Jul. 30, 2003.
Patent Abstracts of Japan for JP2003-315998 published Nov. 6, 2003.
Kilambi H et al., "Influence of molecular dipole on monoacrylate monomer reactivity", Polymer, Elsevier Science Publishers B.V, GB, vol. 46, No. 13, (Jun. 17, 2005), pp. 4735-4742, XP004904221 ISSN: 0032-3861.
European Search Report Dated Mar. 3, 2006; Application No. 05256674.2-2103.

*Primary Examiner*—Helen L. Pezzuto
(74) *Attorney, Agent, or Firm*—Fish & Richardson P.C.

(57) ABSTRACT

The present invention provides compounds having in their molecule a structure contributing to high hydrophilicity, and having high photopolymerizability, as well as polymers of such compounds, and a method for producing the compound. The compounds are diol (meth)acrylate having a urethane bond represented by the formula (1), and cyclic ketal (meth) acrylate having a urethane bond represented by the formula (2):

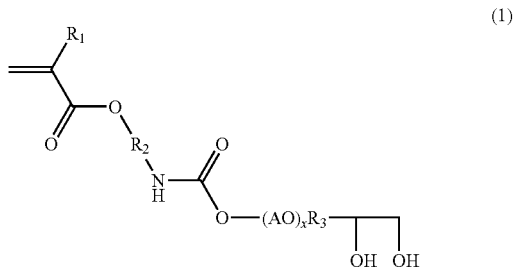

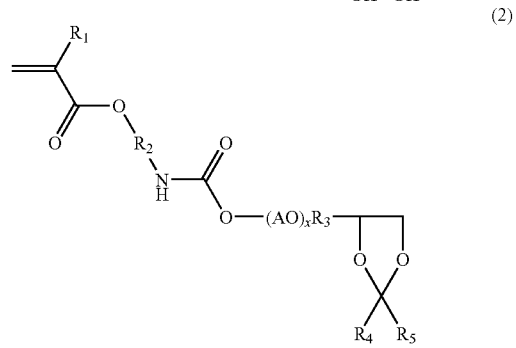

($R_1$: H, —$CH_3$; $R_2$: —($CH_2$)n-; $R_3$: —($CH_2$)m-; n: 1-4; m: 1-8; (AO): C2-C4 oxyalkylene group; x: 0-1000; $R_4$, $R_5$: H, —$CH_3$, —$C_2H_5$).

5 Claims, 1 Drawing Sheet

DIOL (METH) ACRYLATE COMPOUND HAVING URETHANE BOND, METHOD FOR PRODUCING THE SAME, AND POLYMER THEREOF

CROSS REFERENCE TO PRIOR APPLICATIONS

This application is a divisional of U.S. patent application Ser. No. 12/478,189, filed on Jun. 4, 2009, now U.S. Pat. No. 7,649,105, which is a divisional of U.S. patent application Ser. No. 11/259,543, filed Oct. 25, 2005, now U.S. Pat. No. 7,557,239.

BACKGROUND OF THE INVENTION

1. Field of the Invention

The present invention relates to a novel diol (meth)acrylate compound having a urethane bond that is widely useful in the fields of coatings, adhesives, shapable materials, inks, printing materials, electrical insulating materials, optical materials, dental materials, medical materials, or the like, as well as a polymer of the compound and a method for producing the compound. The present invention also relates to a cyclic ketal (meth)acrylate compound having a urethane bond and a polymer thereof that find one of their applications as a starting material for the manufacture of the above-mentioned diol (meth)acrylate compound having a urethane bond and a polymer thereof.

2. Description of Related Art (Meth)acrylate monomers, which are known to have high reactivity, are used alone or in copolymerization with another ethylenic unsaturated compound, for producing polymer compounds that are highly versatile and capable of meeting various demands, with the aid of heat, UV rays, electron beams, or radical polymerization initiators. Such (meth)acrylate monomers are used not only in the fields of adhesives and coatings, for example, but also have recently come to be used in the fields of electronic and dental materials. In the field of medical materials, in particular, hydrophilic (meth)acrylate compounds, such as hydroxyethylmethacrylate, glycerol methacrylate, and vinylpyrrolidone, have been proposed and are already in practical use.

As the (meth)acrylate monomers have come to be used in the fields of electronic and dental materials, which require high purity and performance for the materials, the monomers are now desired to meet new demands, including excellent affinity to non-aqueous materials, adhesivity, and hydrophilicity, as well as functionality such as photopolymerizability.

Examples of (meth)acrylate monomers that could meet such demands include a phosphorous-containing urethane (meth)acrylate compound as proposed in JP-2003-212954-A, and a photosensitive composition containing polyfunctional urethane acrylate having a (meth)acryloyl group proposed as a color filter material in JP-2003-315998-A.

However, there still remain problems in polymerizability of the monomers or the composition, adhesivity to a substrate when used in a resist, and easiness of synthesis, which problems have not been solved sufficiently. Therefore, development of novel (meth)acrylate monomers is eagerly demanded that are excellent in photopolymerizability, adhesivity, and easiness of manufacture.

BRIEF SUMMARY OF THE INVENTION

It is therefore an object of the present invention to provide a diol (meth)acrylate compound having a urethane bond that has in its molecule a structure contributing to high hydrophilicity and has high photopolymerizability, as well as a polymer of such a compound.

It is another object of the present invention to provide a method for easily producing the above diol (meth)acrylate compound having a urethane bond.

It is yet another object of the present invention to provide a cyclic ketal (meth)acrylate compound having a urethane bond and a polymer thereof that may find one of their applications as a starting material for the above diol (meth)acrylate compound having a urethane bond and a polymer thereof.

The present inventors have made intensive researches for achieving the above objects, to find out that a diol (meth)acrylate compound having a urethane bond which has in its molecule a hydrophilic (meth)acrylate group, a hydrophilic urethane bond, and a plurality of hydroxyl groups, is the monomer that could achieve the above objects, thereby completing the present invention.

According to the present invention, there is provided a diol (meth)acrylate compound having a urethane bond represented by the formula (1) (abbreviated as compound (1) hereinbelow):

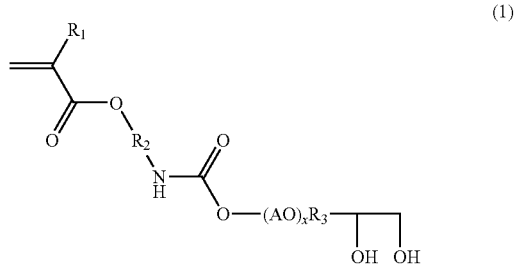

(1)

wherein $R_1$ stands for a hydrogen atom or a methyl group, $R_2$ stands for $-(CH_2)n-$, and $R_3$ stands for $-(CH_2)m-$, provided that n is an integer of 1 to 4 and m is an integer of 1 to 8; (AO) stands for an oxyalkylene group having 2 to 4 carbon atoms, and x is an integer of 0 to 1000.

According to the present invention, there is also provided a cyclic ketal (meth)acrylate compound having a urethane bond represented by the formula (2) (abbreviated as compound (2) hereinbelow):

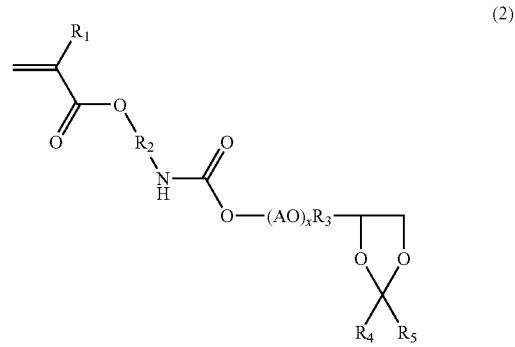

(2)

wherein $R_1$ to $R_3$, (AO), and x are the same as those in the formula (1); $R_4$ and $R_5$ may either be the same or different, and each stands for a hydrogen atom, a methyl group, or an ethyl group.

According to the present invention, there is further provided a method for preparing compound (1) comprising the steps of:

(a) subjecting a cyclic ketal represented by the formula (3) and a (meth)acryloyloxyalkyl isocyanate represented by the formula (4) to urethane reaction to obtain compound (2):

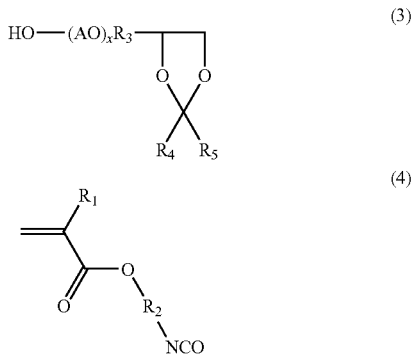

wherein $R_1$ to $R_5$, (AO), and x are the same as those in the formulae (1) and (2), and (b) subjecting compound (2) to hydrolytic ring-opening in a water-containing solvent in the presence of a catalyst.

According to the present invention, there are further provided polymers obtained by polymerizing a polymerizable material comprising compound (1) (sometimes referred to as polymerizable material (1) hereinbelow) or a polymerizable material comprising compound (2) (sometimes referred to as polymerizable material (2) hereinbelow).

DETAILED DESCRIPTION OF THE INVENTION

Figure 1:
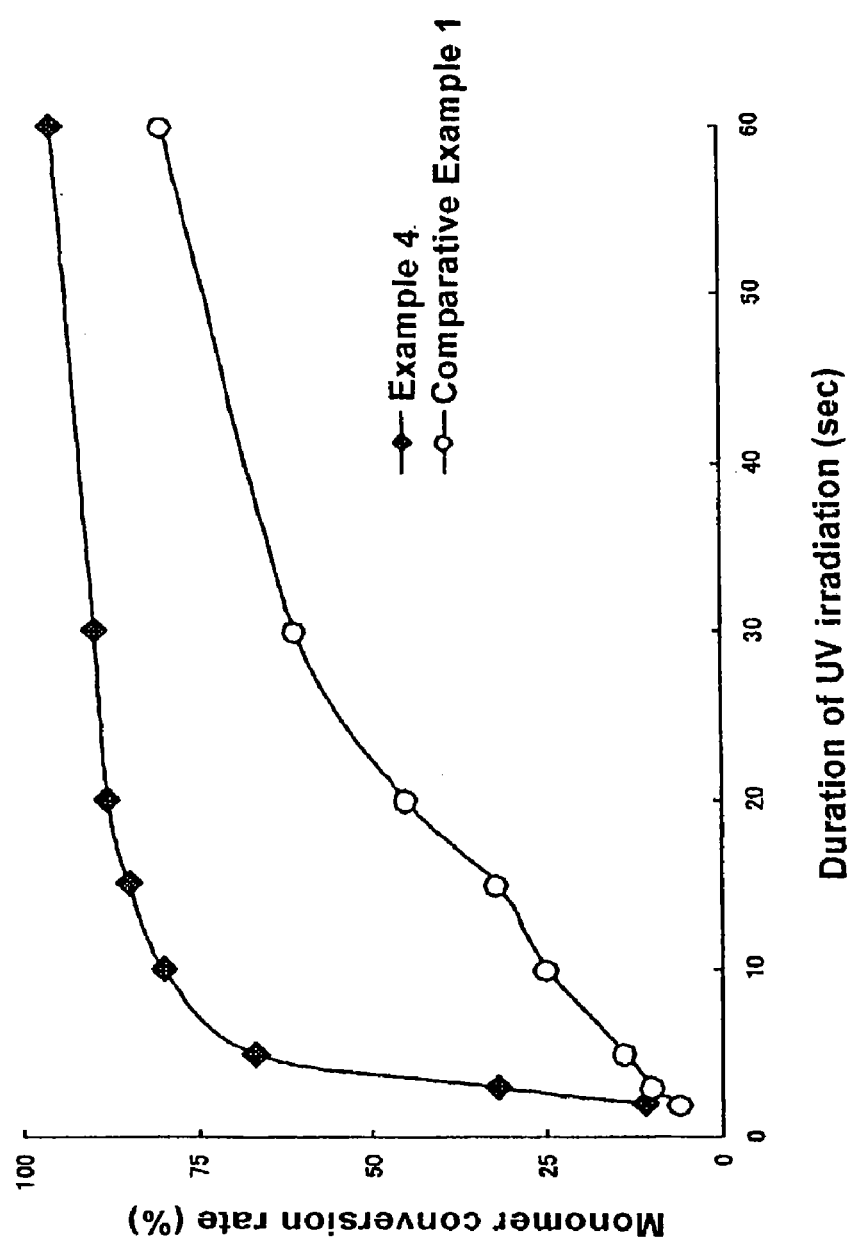
FIG. 1 is a graph showing the photopolymerizability of glyceryl-1-methacryloyloxyethyl urethane and glyceryl-1-methacrylate.

The present invention will now be explained in detail.

Compound (1) according to the present invention is a diol (meth)acrylate compound having a urethane bond represented by the formula (1). Compound (2) according to the present invention is a cyclic ketal (meth)acrylate compound having a urethane bond represented by the formula (2).

In the formulae (1) and (2), $R_1$ stands for a hydrogen atom or a methyl group, with a hydrogen atom being preferred for higher photopolymerizability. $R_2$ stands for a group represented by —$(CH_2)_n$-, wherein n is an integer of 1 to 4. Specifically, $R_2$ stands for —$CH_2$—, —$CH_2CH_2$—, —$CH_2CH_2CH_2$—, or —$CH_2CH_2CH_2CH_2$—, with —$CH_2CH_2$— being preferred for availability. $R_3$ stands for a group represented by —$(CH_2)_m$-, wherein m is an integer of 1 to 8. $R_3$ may specifically be, for example, —$CH_2$—, —$CH_2CH_2$—, —$CH_2CH_2CH_2$—, or —$CH_2CH_2CH_2CH_2$—, with —$CH_2$— being preferred for availability. (AO) stands for an oxyalkylene group having 2 to 4 carbon atoms, and may specifically be an oxyethylene, oxypropylene, or oxybutylene group. x is an integer of 0 to 1000, preferably 0 to 500 for easiness of synthesis. When x is not 0, (AO)x may preferably be a residue of oxyethylene polymer. In the formula (2), $R_4$ and $R_5$ may either be the same or different, and each stands for a hydrogen atom, a methyl group, or an ethyl group.

Examples of compound (1) may include glyceryl-1-methacryloyloxyethyl urethane, 3,4-dihydroxybutyl-1-methacryloyloxyethyl urethane, 5,6-dihydroxyhexyl-1-methacryloyloxyethyl urethane, glycerine-α-monopolyethylene glycol-1-methacryloyloxyethyl urethane, and glycerine-α-monopolypropylene glycol-1-methacryloyloxyethyl urethane, with glyceryl-1-methacryloyloxyethyl urethane being preferred for its synthesizability.

Compound (2) may find one of its applications as a precursor of compound (1) in the preparation method of the present invention to be discussed later. Specific examples of this compound may include 2,3-O-isopropylideneglyceryl-1-methacryloyloxyethyl urethane, 3,4-O-isopropylidenebutyl-1-methacryloyloxyethyl urethane, 5,6-O-isopropylidenehexyl-1-methacryloyloxyethyl urethane, 2,3-O-sec-butylideneglyceryl-1-methacryloyloxyethyl urethane, 3,4-O-sec-butylidenebutyl-1-methacryloyloxyethyl urethane, 5,6-O-sec-butylidenehexyl-1-methacryloyloxyethyl urethane, 2,3-O-isopropylideneglycerine-α-monopolyethylene glycol-1-methacryloyloxyethyl urethane, and 2,3-O-isopropylideneglycerine-α-monopolypropylene glycol-1-methacryloyloxyethyl urethane, with 2,3-O-isopropylideneglyceryl-1-methacryloyloxyethyl urethane being preferred for its easiness of reaction.

Compound (1) of the present invention may be prepared, for example, by the method of the present invention including the steps of:

(a) subjecting a cyclic ketal represented by the formula (3) and a (meth)acryloyloxyalkyl isocyanate represented by the formula (4) to urethane reaction to obtain compound (2), and (b) subjecting compound (2) to hydrolytic ring-opening in a water-containing solvent in the presence of a catalyst.

In the formula (3), $R_4$ and $R_5$ may either be the same or different, and each stands for a hydrogen atom, a methyl group, or an ethyl group, with a methyl group being preferred for easiness of removal of residual cyclic ketal after the reaction.

Examples of the cyclic ketal represented by the formula (3) may include 2,3-O-isopropylideneglycerol, 3,4-O-isopropylidenebutanol, 5,6-O-isopropylidenehexanol, 2,3-O-sec-butylideneglycerol, 3,4-O-sec-butylidenebutanol, 5,6-O-sec-butylidenehexanol, 2,3-O-isopropylideneglycerine-α-monopolyethyleneglycol, and 2,3-O-isopropylideneglycerine-α-monopolypropylene glycol, with 2,3-O-isopropylideneglycerol being preferred for its easiness of reaction.

Such a cyclic ketal may be obtained commercially, or synthesized by subjecting glycerine and a carbonyl compound represented by the formula (5) to ring formation in a solvent, such as petroleum ether, benzene, or toluene, in the presence of a catalyst, such as hydrochloric acid, sulfuric acid, or p-toluene sulfonic acid:

wherein $R_4$ and $R_5$ are the same as those in the formula (3).

Examples of the carbonyl compound represented by the formula (5) may include formaldehyde, acetaldehyde, acetone, methyl ethyl ketone, and 3-pentanone, with acetone being preferred for its easiness of removal after reaction.

In the urethane reaction followed by preparation of a polymer, if the cyclic ketal represented by the formula (3) is replaced with a compound having three hydroxyl groups in a molecule, for example, glycerine, which has not been subjected to ring formation, the reaction mass will be gelated, failing to result a polymer.

Among the cyclic ketals, cyclic ketal glycerine-α-monopolyalkylene glycol may effectively be prepared, for example, by a method proposed in JP-6-145341-A, namely, by adding alkylene oxide having 2 to 4 carbon atoms to isopropylidene glycerol.

In the formula (4) above, $R_1$ and $R_2$ are the same as those in the formula (1). Examples of the (meth)acryloyloxyalkyl isocyanate represented by the formula (4) may include methacryloyloxyethyl isocyanate and methacryloyloxypropyl isocyanate, with methacryloyloxyethyl isocyanate being preferred for its availability. The isocyanate may be obtained commercially, or may be synthesized from known materials by combining known processes.

In step (a) of the above method, the amount of the cyclic ketal represented by the formula (3) for the urethane reaction may preferably be 1.1 to 3 times the amount of the (meth) acryloyloxyakyl isocyanate in molar ratio. The urethane reaction proceeds without a catalyst, but in order to shorten the reaction time, it is preferred to use a catalyst.

Examples of the catalyst may include tertiary amine compounds, such as N-methylmorpholine, N-ethylmorpholine, dimorpholinomethane, ethyl morpholinoacetate, N-(3-dimethylaminopropyl)morpholine, N-methylpiperidine, quinoline, 1,2-dimethylimidazole, N-methyldicyclohexylamine, triethylamine, pyridine, 1,4-diazabicyclooctane, tetramethyl-1,3-butanediamine, tetramethyl-1,3-propanediamine, dimethyldiethyl-1,3-propanediamine, pentamethyldiethylenediamine, tetraethylmethanediamine, bis(2-dimethylaminoethyl)adipate, bis(2-diethylaminoethyl) adipate, dimethylcyclohexylamine, diethylcyclohexylamine, methyloctylcyclohexylamine, and methyldodecylcyclohexylamine; and tin-containing compounds, such as tin chloride, tetra-n-butyltin, tetraphenyltin, tri-n-butyltin acetate, dimethyldichlorotin, di-n-butyltin diacetate, di-n-butyldichlorotin, di-n-butyltin dilaurate, di-n-butyltin dilaurylmercaptide, bis (2-ethylhexyl)tin oxide, and di-n-butyltin sulfide. Tertiary amine compounds are preferred since these compounds are safer even when they are contained in the reaction product as a residual catalyst.

The amount of the catalyst, when used, is usually 0.001 to 50 parts by weight, preferably 0.01 to 30 parts by weight, most preferably 0.1 to 10 parts by weight, based on 100 parts by weight of (meth)acryloyloxyalkyl isocyanate.

There is no problem even if the urethane reaction in step (a) is performed without a solvent, or the reaction may alternatively be performed in the presence of a solvent, if the solvent is not reactive to (meth)acryloyloxyalkyl isocyanate. Examples of such a solvent may include acetone, methyl ethyl ketone, acetonitrile, chloroform, carbon tetrachloride, dichloromethane, benzene, toluene, hexane, and pyridine, with acetone being the most preferred for its easiness of removal after the reaction.

The amount of the solvent, when used, is about 0.1 to 1000 parts by weight, based on 100 parts by weight of (meth) acryloyloxyalkyl isocyanate.

The temperature for the urethane reaction is usually 0 to 100° C., preferably 25 to 80° C., most preferably 40 to 60° C. If the reaction temperature is lower than 0° C., the reaction may require a prolonged period of time to complete. If the reaction temperature is higher than 100° C., side reactions, such as polymerization, are likely to occur. The reaction time may vary depending on the reaction temperature, the kind and amount of a catalyst, but a preferred reaction time is usually about 6 to 24 hours.

Through step (a), compound (2) as a precursor of compound (1) is obtained. Compound (2) may be used as it is without purification, or after isolation and purification by treatments, such as drying under reduced pressure, as a material to be subjected to step (b) for obtaining compound (1), or subjected to preparation of a polymerizable material containing compound (2) to be discussed later.

According to the present invention, the precursor, compound (2), is subjected to hydrolytic ring-opening in a water-containing solvent in the presence of a catalyst in step (b) to obtain the objective compound (1).

The catalyst for the hydrolytic ring-opening may preferably be, for example, inorganic acid, such as hydrochloric, sulfuric, or phosphoric acid; or organic acid, such as p-toluene sulfonic acid, with hydrochloric acid being particularly preferred for its easiness of removal after the reaction. A preferred amount of the catalyst is usually 0.1 to 10.0 wt % of the overall reaction system.

Examples of the water-containing solvent used in the hydrolytic ring-opening may include water alone, or a mixed solvent of water and a water-soluble solvent, such as methanol, ethanol, isopropanol, tetrahydrofuran (THF), acetonitrile, acetone, methyl ethyl ketone, dimethylformamide, dimethylsulfoxide, and dimethylacetamide. A methanol/water mixed solvent is the most preferred for its easiness of removal after the reaction.

The temperature for the hydrolytic ring-opening is preferably in the range of 0 to 50° C. If the temperature is higher than 50° C., side reactions, such as hydrolysis of ester or ester exchange reaction, may occur. If the temperature is lower than 0° C., the moisture may disadvantageously be solidified. The reaction time may vary depending on the reaction temperature, the kind and amount of the catalyst, but may preferably be about 1 to 6 hours.

With the progress of hydrolytic ring-opening, a carbonyl compound may be generated as a by-product in the reaction system. Such a by-product carbonyl compound is preferably removed from the reaction system by means of vacuum distillation or the like in order to shorten the reaction time.

Compound (1) prepared by the method of the present invention may be used as it is without purification, or after isolation and purification by means of drying under reduced pressure, recrystallization, or columns, for preparing a polymerizable material to be discussed later.

The polymers of the present invention are obtained by polymerizing polymerizable material (1) containing compound (1) or polymerizable material (2) containing compound (2).

The polymer obtained by polymerizing polymerizable material (1) containing compound (1) may alternatively be obtained by subjecting compound (2), which has been obtained by polymerizing polymerizable material (2) containing compound (2), to hydrolytic ring-opening with acid.

The molecular weight of the polymers of the present invention is not particularly limited, and may suitably be selected for exhibiting properties required for each application, by adjusting the polymerization conditions or the like factors. Usually, the present polymers may have a weight average molecular weight of about 5000 to 1000000.

Polymerizable material (1) may be composed solely of compound (1), or in mixture with other monomers copolymerizable with compound (1).

Examples of such other monomers may include various (meth)acrylates, such as diethylaminoethyl(meth)acrylate, polyethylene glycol mono(meth)acrylate, glycerol (meth)acrylate, (meth)acryloyloxyethyl phosphate, (meth)acryloyloxyethyl phosphorylcholine, methyl(meth)acrylate, glycidyl(meth)acrylate, dimethylaminoethyl(meth)acrylate, 2-hydroxyethyl(meth)acrylate, and 2-methoxyethyl(meth) acrylate; various vinyl ethers, such as methyl vinyl ether; and various other radical polymerizable monomers, such as acrylamide, N,N'-dimethylacrylamide, (meth)acrylic acid, allyl alcohol, acrylonitrile, acrolein, vinyl acetate, sodium vinylsulfonate, styrene, chlorostyrene, vinylphenol, vinylcinnamate, vinyl chloride, vinyl bromide, butadiene, vinylene carbonate, itaconic acid, itaconates, fumaric acid, fumarates, maleic acid, and maleates. Among these, 2-hydroxyethylmethacrylate is preferred for its compatibility. For easy preparation of the polymer, polymerizable material (1) is preferably composed solely of compound (1).

The amount of the other monomers, when used, in polymerizable material (1) may arbitrarily and suitably be selected. For bringing out its performance, compound (1) is preferably contained in polymerizable material (1) in an amount of not less than 10 wt %.

Polymerizable material (1) may be subjected to polymerization in bulk, or in mixture with a solution. Examples of such a solution may include methanol, ethanol, isopropanol, dimethylformamide, dimethylsulfoxide, dimethylacetamide, mixtures of water and such organic solvents, and various other polar solvents, with methanol being preferred for its chain transfer coefficient.

Polymerizable material (1) may be polymerized by radical polymerization or photopolymerization.

Radical polymerization may be performed using a radical initiator. Examples of a radical initiator may include organic peroxides, such as benzoyl peroxide and t-butylperoxy neodecanoate; and azo compounds, such as 2,2'-azobisisobutyronitrile and 2,2'-azobisdimethylisobutyrate, with 2,2'-azobisdimethylisobutyrate being preferred in view of the workability and insolubilization of the resulting polymer.

The amount of the radical initiator may preferably be 0.1 to 5.0 parts by weight, based on 100 parts by weight of polymerizable material (1). The temperature and time for the polymerization may suitably be selected depending on the kind of the radical initiator, presence/absence or the kind of other monomers. For example, for polymerizing polymerizable material (1) composed solely of compound (1) using 2,2'-azobisdimethylisobutyrate as a radical initiator, suitable temperature and time for the polymerization are preferably 50 to 70° C. and about 8 to 48 hours, respectively.

The photopolymerization may be performed by irradiation with UV at a wavelength of 254 nm or electron beam (EB) at an accelerating voltage of 150 to 300 kV. Use of a photopolymerization initiator is optional, but preferred in view of the reaction time.

Examples of the photopolymerization initiator may include 2-hydroxy-2-methyl-1-phenyl-1-propanone and 1-hydroxy-cyclohexylphenyl ketone, with 2-hydroxy-2-methyl-1-phenyl-1-propanone being preferred for its solubility.

Polymerizable material (2) may be composed solely of compound (2) or in mixture with other monomers copolymerizable with compound (2). Polymerization of polymerizable material (2) composed solely of compound (2) results in a hydrophobic polymer, but this polymer may be given hydrophilicity by subjecting the polymer to hydrolytic ring-opening. On the other hand, compound (2) per se has good copolymerizability with hydrophobic monomers, and thus may be used in mixture with hydrophobic monomers, which are usually hard to be copolymerized with hydrophilic monomers. In this case, compound (2) may act as a hydrophilizer of polymerizable material (2) to give a hydrophilic polymer.

Examples of the other monomers in polymerizable material (2) may include various (meth)acrylates, such as diethylaminoethyl(meth)acrylate, polyethylene glycol mono(meth) acrylate, glycerol (meth)acrylate, (meth)acryloyloxyethyl phosphate, (meth)acryloyloxyethyl phosphorylcholine, methyl(meth)acrylate, glycidyl(meth)acrylate, dimethylaminoethyl(meth)acrylate, 2-hydroxyethyl(meth)acrylate, and 2-methoxyethyl(meth)acrylate; various vinyl ethers, such as methyl vinyl ether; and various other radical polymerizable monomers, such as acrylamide, N,N'-dimethylacrylamide, (meth)acrylic acid, allyl alcohol, acrylonitrile, acrolein, vinyl acetate, sodium vinylsulfonate, styrene, chlorostyrene, vinylphenol, vinylcinnamate, vinyl chloride, vinyl bromide, butadiene, vinylene carbonate, itaconic acid, itaconates, fumaric acid, fumarates, maleic acid, and maleates. Among these, methylmethacrylate is preferred for its compatibility. For easy preparation of the polymer, polymerizable material (2) is preferably composed solely of compound (2).

The amount of the other monomers, when used, in polymerizable material (2) may arbitrarily and suitably be selected. For bringing out its performance, compound (2) is preferably contained in polymerizable material (2) in an amount of not less than 10 wt %.

Polymerizable material (2) may be subjected to polymerization in bulk, or in mixture with a solution. Examples of such a solution may include benzene, toluene, acetone, methyl ethyl ketone, chloroform, dichloromethane, and carbon tetrachloride solvents, with benzene being preferred for its chain transfer coefficient.

Polymerizable material (2) may be polymerized by radical polymerization or photopolymerization.

Radical polymerization may be performed using a radical initiator. Examples of a radical initiator may include organic peroxides, such as benzoyl peroxide and bis(4-t-butylcyclohexyl)peroxydicarbonate; and azo compounds, such as 2,2'-azobisisobutyronitrile and 2,2'-azobisdimethylisobutyrate, with 2,2'-azobisdimethylisobutyrate being preferred in view of the workability and insolubilization of the resulting polymer.

The amount of the radical initiator may preferably be 0.1 to 5.0 parts by weight, based on 100 parts by weight of polymerizable material (2). The temperature and time for the polymerization may suitably be selected depending on the kind of the radical initiator, presence/absence or the kind of other monomers. For example, for polymerizing polymerizable material (2) composed solely of compound (2) using 2,2'-azobisdimethylisobutyrate as a radical initiator, suitable temperature and time for the polymerization are preferably 50 to 70° C. and about 8 to 48 hours, respectively.

The photopolymerization may be performed by irradiation with UV at a wavelength of 254 nm or electron beam (EB) at an accelerating voltage of 150 to 300 kV. Use of a photopolymerization initiator is optional, but preferred in view of the reaction time.

Examples of the photopolymerization initiator may include 2-hydroxy-2-methyl-1-phenyl-1-propanone and 1-hydroxy-cyclohexylphenyl ketone, with 2-hydroxy-2-methyl-1-phenyl-1-propanone being preferred for its solubility.

A polymer obtained by polymerizing polymerizable material (2) composed solely of compound (2) may be produced into a polymer similar to the polymer obtained by polymerizing polymerizable material (1) composed solely of compound (1), in accordance with the method for ring-opening compound (2) as a precursor in the method of the present invention, i.e. hydrolytic ring-opening with acid, for example, hydrolytic ring-opening in a water-containing solvent in the presence of a catalyst.

The polymers of the present invention obtained by polymerizing polymerizable material (1) or (2) may be formed into films or pellets by conventional processes, and these may be used as materials for coatings, optical materials, dental materials, electronic materials, printing materials, or the like materials.

Compounds (1) and (2) of the present invention have a hydrophilic urethane bond in the molecular structure of the (meth)acrylate compound, and compound (1) additionally has hydroxyl groups, so that these compounds are excellently photopolymerizable, and expected to further have hydrophilicity and adhesivity. Thus these compounds and polymers thereof are expected to provide applications as raw materials or stock materials in a variety of fields including the medical field. In particular, compound (2) may also find one of its applications as a precursor for compound (1), and the polymer obtained by polymerization of polymerizable material (2) containing compound (2) may be produced into a polymer similar to the polymer obtained by polymerization of polymerizable material (1) containing compound (1), by hydrolytic ring-opening with acid.

In the method for preparing compound (1) according to the present invention, the reaction path is employed wherein compound (2) is used as a precursor, so that preparation of the objective compound (1) is facilitated.

EXAMPLES

The present invention will now be explained in more detail with reference to Examples, which are illustrative only and are not intended to limit the present invention.

Preparation Example 1

Synthesis of Compound Represented by Formula (3)

2,3-O-isopropylideneglycerol was prepared by the following synthesis process in accordance with the method described in M. Renoll, M. S. Newman, Org. Syn. Coll. 3, 502 (1955).

In a pear-shaped flask equipped with a calcium tube, a condenser, and a Dean-Stark trap, 100 g of glycerine, 300 ml of acetone, 3 g of p-toluenesulfonic acid monohydrate, and 300 ml of petroleum ether were placed, and heated to reflux in an oil bath set at 50° C. After 12 hours, when about 23 ml of water was collected and no further formation of water was confirmed, the reaction mixture was cooled to room temperature. 3 g of sodium acetate was added, and the mixture was stirred for 30 minutes. Petroleum ether and acetone were distilled off in an evaporator. The resulting crude product was purified by vacuum distillation to give 130.6 g of 2,3-O-isopropylideneglycerol in the form of colorless, transparent liquid at 91% yield. $^1$H-NMR spectral data are shown below:

$^1$H-NMR(CDCl$_3$) 1.3-1.5 ppm, d, C$\underline{H}_3$(6H) 1.9 ppm, s, O$\underline{H}$(1H) 3.5-4.3 ppm, m, C$\underline{H}_2$C$\underline{H}$C$\underline{H}_2$(5H)

Preparation Example 2

Synthesis of Compound Represented by Formula (3)

The process of Preparation Example 1 was generally repeated, except that acetone was replaced with methyl ethyl ketone, to give 139.6 g of 2,3-O-sec-butylideneglycerol in the form of colorless, transparent liquid at 88% yield. $^1$H-NMR spectral data are shown below:

$^1$H-NMR(CDCl$_3$) 0.8-1.0 ppm, t, CH$_2$C$\underline{H}_3$(3H) 1.2-1.4 ppm, d, C$\underline{H}_3$(3H) 1.6-1.8 ppm, q, C$\underline{H}_2$CH$_3$(2H) 1.9 ppm, s, O$\underline{H}$(1H) 3.5-4.3 ppm, m, C$\underline{H}_2$C$\underline{H}$C$\underline{H}_2$(5H)

Preparation Example 3

Synthesis of Compound Represented by Formula (3)

2,3-O-isopropylideneglycerine-α-monopolyethylene glycol was prepared by the following synthesis process in accordance with the method described in JP-6-145341-A.

13.2 g (0.1 mole) of isopropylidene glycerol and 0.2 g of potassium hydroxide were placed in a 1 L autoclave, which was flushed with nitrogen gas and heated to 100° C. Under the conditions of 100 to 150° C. and 10 kg/cm$^2$ or lower, 230 g (5.22 mole) of ethylene oxide was added over 3 hours, and the reaction was continued for further 1 hour. The reaction system was cooled to 60° C. while the unreacted ethylene oxide was removed by evaporation in a stream of nitrogen. Then acetic acid was added to adjust the pH of the reaction mixture to 7.0, and the reaction mixture was heated at 100° C. at 100 mmHg or lower for 1 hour to distill off water. The precipitated salt was filtered out to give 197.3 g of 2,3-O-isopropylideneglycerine-α-monopolyethylene glycol. $^1$H-NMR spectral data are shown below:

$^1$H-NMR(CDCl$_3$) 1.3-1.5 ppm, d, C$\underline{H}_3$(6H) 1.9 ppm, s, O$\underline{H}$(1H) 3.4-4.3 ppm, m, (C$\underline{H}_2$C$\underline{H}_2$O)$_{48}$, C$\underline{H}_2$C$\underline{H}$C$\underline{H}_2$(197H)

Example 1

Synthesis of Compound (2)

In a pear-shaped flask, 6.60 g of 2,3-O-isopropylideneglycerol synthesized in Preparation Example 1 and 1 ml of pyridine were placed, 7.37 g of methacryloyloxyethyl isocyanate (manufactured by SHOWA DENKO K.K.) was measured out, and a dropping funnel and a calcium tube were installed on the flask. The methacryloyloxyethyl isocyanate was added slowly dropwise at room temperature in dark, and reacted in an oil bath set at 50° C. for 7 hours. After the reaction was completed, pyridine and excess 2,3-O-isopropylideneglycerol were distilled off in vacuo to give 12.7 g of 2,3-O-isopropylideneglyceryl-1-methacryloyloxyethyl urethane in the form of white solid at 93% yield. $^1$H-NMR spectral data are shown below:

$^1$H-NMR (CDCl$_3$) 1.3-1.5 ppm, d, C$\underline{H}_3$(6H) 1.9 ppm, s, CH$_2$=CH(C$\underline{H}_3$)(3H) 3.4-4.4 ppm, m, OC$\underline{H}_2$CH$_2$NH C$\underline{H}_2$C$\underline{H}$C$\underline{H}_2$(9H) 5.1 ppm, s, N$\underline{H}$(1H) 5.6, 6.1 ppm, s, C$\underline{H}_2$=C(CH$_3$)(2H)

The resulting product was analyzed by HPLC under the following conditions to confirm that the purity of the obtained 2,3-O-isopropylideneglyceryl-1-methacryloyloxyethyl urethane was not lower than 98%.

(Conditions of HPLC)

Eluent: water/acetonitrile=4/6 (v/v); Column: ODS; Detector: UV (220 nm); Flow rate: 1.0 ml/min; Column oven temperature: 40° C.

Example 2

Synthesis of Compound (2)

The process of Example 1 was generally repeated, except that 2,3-O-isopropylideneglycerol was replaced with 2,3-O- sec-butylideneglycerol synthesized in Preparation Example 2, to give 13.8 g of 2,3-O-sec-isobutylideneglyceryl-1-methacryloyloxyethyl urethane in the form of colorless, transparent liquid at 96% yield. $^1$H-NMR spectral data are shown below:

$^1$H-NMR (CDCl$_3$) 0.8-1.0 ppm, t, CH$_2$C$\underline{H}_3$(3H) 1.2-1.4 ppm, d, C$\underline{H}_3$(3H) 1.6-1.8 ppm, q, C$\underline{H}_2$CH$_3$(2H) 1.9 ppm, s, CH$_2$=CH(C$\underline{H}_3$)(3H) 3.4-4.4 ppm, m, OC$\underline{H}_2$CH$_2$NH C$\underline{H}_2$CHCH$_2$(9H) 5.1 ppm, s, N$\underline{H}$(1H) 5.6, 6.1 ppm, s, C$\underline{H}_2$=C(CH$_3$)

The resulting product was analyzed by HPLC in the same way as in Example 1 to confirm that the purity of the obtained 2,3-O-sec-isobutylideneglyceryl-1-methacryloyloxyethyl urethane was not lower than 97%.

Example 3

Synthesis of Compound (2)

The process of Example 1 was generally repeated, except that 2,3-O-isopropylideneglycerol was replaced with 2,3-O-isopropylideneglycerine-α-monopolyethylene glycol synthesized in Preparation Example 3, to give 21.3 g of 2,3-O-isopropylideneglycerine-α-monopolyethylene glycol-1-methacryloyloxyethyl urethane in the form of white solid at 96% yield. $^1$H-NMR spectral data are shown below:

$^1$H-NMR (CDCl$_3$) 1.3-1.5 ppm, d, C$\underline{H}_3$(6H) 1.9 ppm, s, CH$_2$=CH(C$\underline{H}_3$)(3H) 3.4-4.5 ppm, m, OC$\underline{H}_2$CH$_2$NH(C$\underline{H}_2$CH$_2$O)$_{48}$C$\underline{H}_2$CHCH$_2$(201H) 5.1 ppm, s, N$\underline{H}$(1H) 5.6, 6.1 ppm, s, C$\underline{H}_2$=C(CH$_3$)(2H)

The resulting product was analyzed by HPLC in the same way as in Example 1 to confirm that the purity of the obtained 2,3-O-isopropylideneglycerine-α-monopolyethylene glycol-1-methacryloyloxyethyl urethane was not lower than 96%.

Example 4

Synthesis and Photopolymerization Test of Compound (1)

In a vial, magnetic stirrers, 1.0 g of 2,3-O-isopropylideneglyceryl-1-methacryloyloxyethyl urethane synthesized in Example 1, 3.9 ml of methanol, and 100 μl of 4N hydrochloric acid were placed, and reacted under stirring at room temperature for 30 minutes. As a result, the mixture was turned from a suspension to a clear solution. The mixture was further reacted under stirring for 60 minutes and vacuum dried, to give 852 mg of glyceryl-1-methacryloyloxyethyl urethane in the form of colorless, viscous liquid. $^1$H-NMR spectral data are shown below:

$^1$H-NMR (D$_2$O) 1.8 ppm, s, CH$_2$=CH(C$\underline{H}_3$)(3H) 3.3-4.2 ppm, m, OC$\underline{H}_2$CH$_2$NHC$\underline{H}_2$CHCH$_2$(9H) 5.6, 6.0 ppm, s, C$\underline{H}_2$=C(CH$_3$)(2H)

The resulting product was analyzed by HPLC in the same way as in Example 1 to confirm that the purity of the obtained glyceryl-1-methacryloyloxyethyl urethane was not lower than 98%.

The synthesized glyceryl-1-methacryloyloxyethyl urethane was tested for photopolymerizability by the following process.

1.0 g of glyceryl-1-methacryloyloxyethyl urethane, 1 mg of 2-hydroxy-2-methylpropiophenone, and 1 ml of ion-exchanged water were placed in a quartz cell that was transparent on four sides, and irradiated with UV rays from a 400 W high-pressure mercury lamp in an argon atmosphere. A small amount of samples were taken at intervals, and diluted 1000 times with ion-exchanged water. The absorbance of each sample at 220 nm was determined with an absorptiometer to calculate the content of glyceryl-1-methacryloyloxyethyl urethane monomer.

The relationship between the duration of UV irradiation and the monomer conversion rate of the obtained glyceryl-1-methacryloyloxyethyl urethane are shown in FIG. 1.

Comparative Example 1

The measurement of Example 4 was generally repeated, except that glyceryl-1-methacryloyloxyethyl urethane was replaced with glyceryl-1-methacrylate to determine the relationship between the duration of UV irradiation and the monomer conversion rate of glyceryl-1-methacrylate. The results are shown in FIG. 1.

From FIG. 1, it is seen that glyceryl-1-methacryloyloxyethyl urethane has far more excellent photopolymerizability than glyceryl-1-methacrylate.

Example 5

Synthesis of Compound (1)

The process of Example 4 was generally repeated, except that 2,3-O-isopropylideneglyceryl-1-methacryloyloxyethyl urethane was replaced with 2,3-O-sec-butylideneglyceryl-1-methacryloyloxyethyl urethane synthesized in Example 2, to give 800 mg of glyceryl-1-methacryloyloxyethyl urethane in the form of colorless, viscous liquid. $^1$H-NMR spectral data are shown below:

$^1$H-NMR (D$_2$O) 1.8 ppm, s, CH$_2$=CH(C$\underline{H}_3$)(3H) 3.3-4.2 ppm, m, OC$\underline{H}_2$CH$_2$NHC$\underline{H}_2$CHCH$_2$(9H) 5.6, 6.0 ppm, s, C$\underline{H}_2$=C(CH$_3$)(2H)

The resulting product was analyzed by HPLC in the same way as in Example 1 to confirm that the purity of the obtained glyceryl-1-methacryloyloxyethyl urethane was not lower than 97%.

Example 6

Synthesis of Compound (1)

The process of Example 4 was generally repeated, except that 2,3-O-isopropylideneglyceryl-1-methacryloyloxyethyl urethane was replaced with 2,3-O-isopropylideneglycerine-α-monopolyethylene glycol-1-methacryloyloxyethyl urethane synthesized in Example 3, to give 831 mg of glyceryl-α-monopolyethylene glycol-1-methacryloyloxyethyl urethane in the form of white solid. $^1$H-NMR spectral data are shown below:

$^1$H-NMR (D$_2$O) 1.9 ppm, s, CH$_2$=CH(C$\underline{H}_3$)(3H) 3.4-4.4 ppm, m, OC$\underline{H}_2$CH$_2$NH(C$\underline{H}_2$CH$_2$O)$_{48}$C$\underline{H}_2$CHCH$_2$(201H) 5.1 ppm, s, N$\underline{H}$(1H) 5.6, 6.1 ppm, s, C$\underline{H}_2$=C(CH$_3$)(2H)

The resulting product was analyzed by HPLC in the same way as in Example 1 to confirm that the purity of the obtained glyceryl-α-monopolyethylene glycol-1-methacryloyloxyethyl urethane was not lower than 96%.

Example 7

Synthesis of Polymer from Polymerizable Material (1) by Radical Polymerization 1.0 g of glyceryl-1-methacryloyloxyethyl urethane of not lower than 98% purity as synthesized in Example 4, 5 ml of a water/methanol mixed solvent (2/8 (v/v)), and 5 mg of azoisobutyronitrile were measured out and placed in a test tube, and bubbled with argon gas for 30 seconds. The test tube was immediately sealed, and the mixture was reacted for 24 hours at 60° C. After the 24 hours of reaction, the reaction solution was placed in a dialysis membrane (trade name: SPECTRA/PORE 7 (manufactured by FUNAKOSHI CO., LTD.), molecular weight cut-off: 1000), and dialyzed for 12 hours against 1 L of water, which was changed every three hours. 300 ml of the obtained solution was placed in a pear-shaped flask and lyophilized to obtain 890 mg of polyglyceryl-1-methacryloyloxyethyl urethane at 89% yield.

The obtained polymer was easily dissolved in water to give a colorless, viscous solution. This solution was subjected to measurement of the molecular weight by GPC under the following conditions, to confirm that the weight average molecular weight of the polymer was about 56000.

(Conditions of GPC)

Eluent: 20 mM phosphate buffer; Column: TSK gel G4000PW$_{XL}$+TSK gel G2500PW$_{XL}$; Detector: RI; Flow rate: 0.6 ml/min; Column oven temperature: 40° C.; Reference material: polyethylene oxide Example 8

Synthesis of Polymer from Polymerizable Material (2) by Radical Polymerization 1.0 g of 2,3-O-isopropylideneglyceryl-1-methacryloyloxyethyl urethane of not lower than 98% purity as synthesized in Example 1, 5 ml of THF, and 5 mg of azoisobutyronitrile were measured out and placed in a test tube, and bubbled with argon gas for 30 seconds. The test tube was immediately sealed, and the mixture was reacted for 24 hours at 60° C. After the 24 hours of reaction, the reaction solution was cooled down to room temperature, mixed with 1 ml of 4N hydrochloric acid, and stirred for 3 hours. The reaction solution was placed in a dialysis membrane (trade name: SPECTRA/PORE 7 (manufactured by FUNAKOSHI CO., LTD.), molecular weight cut-off: 1000), and dialyzed for 12 hours against 1 L of water, which was changed every three hours. 300 ml of the obtained solution was placed in a pear-shaped flask and lyophilized to obtain 723 mg of polyglyceryl-1-methacryloyloxyethyl urethane at 84% yield.

The obtained polymer was easily dissolved in water to give a colorless, viscous solution. This solution was subjected to measurement of the molecular weight by GPC in the same way as in Example 7, to confirm that the weight average molecular weight of the polymer was about 52000.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A polymer obtained by polymerizing a polymerizable material comprising a cyclic ketal (meth)acrylate compound having a urethane bond represented by the formula (2):

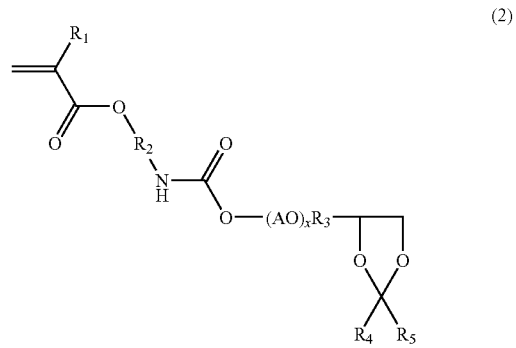

wherein $R_1$ stands for a hydrogen atom or a methyl group, $R_2$ stands for —$(CH_2)n$-, and $R_3$ stands for —$(CH_2)m$-, provided that n is an integer of 1 to 4 and m is an integer of 1 to 8; (AO) stands for an oxyalkylene group having 2 to 4 carbon atoms, x is an integer of 0 to 1000, $R_4$ and $R_5$ may either be the same or different, and each stands for a hydrogen atom, a methyl group, or an ethyl group.

2. The polymer according to claim 1, wherein said cyclic ketal (meth)acrylate compound is selected from the group consisting of
   2,3-O-isopropylideneglyceryl-1-methacryloyloxyethyl urethane,
   3,4-O-isopropylidenebutyl-1-methacryloyloxyethyl urethane,
   5,6-O-isopropylidenehexyl-1-methacryloyloxyethyl urethane,
   2,3-O-sec-butylideneglyceryl-1-methacryloyloxyethyl urethane,
   3,4-O-sec-butylidenebutyl-1-methacryloyloxyethyl urethane,
   5,6-O-sec-butylidenehexyl-1-methacryloyloxyethyl urethane,
   2,3-O-isopropylideneglycerine-α-monopolyethylene glycol-1-methacryloyloxyethyl urethane, and
   2,3-O-isopropylideneglycerine-α-monopolypropylene glycol-1-methacryloyloxyethyl urethane.

3. The polymer according to claim 1, wherein said polymer has a weight average molecular weight of about 5000 to 1000000.

4. The polymer according to claim 1, wherein said polymerizable material consists of said cyclic ketal (meth)acrylate compound.

5. The polymer according to claim 1, wherein said polymerizable material further comprises one or more other monomers copolymerizable with said cyclic ketal (meth) acrylate compound, said other monomers being selected from the group consisting of diethylaminoethyl(meth)acrylate, polyethylene glycol mono(meth)acrylate, glycerol (meth)acrylate, (meth)acryloyloxyethyl phosphate, (meth)acryloyloxyethyl phosphorylcholine, methyl(meth)acrylate, glycidyl(meth)acrylate, dimethylaminoethyl(meth)acrylate, 2-hydroxyethyl(meth)acrylate, 2-methoxyethyl(meth)acrylate, methyl vinyl ether, acrylamide, N,N'-dimethylacrylamide, (meth)acrylic acid, allyl alcohol, acrylonitrile, acrolein, vinyl acetate, sodium vinylsulfonate, styrene, chlorostyrene, vinylphenol, vinylcinnamate, vinyl chloride, vinyl bromide, butadiene, vinylene carbonate, itaconic acid, itaconates, fumaric acid, fumarates, maleic acid, and maleates.

* * * * *